(12) United States Patent
Chomenky et al.

(10) Patent No.: US 6,697,670 B2
(45) Date of Patent: Feb. 24, 2004

(54) APPARATUS AND METHOD FOR REDUCING SUBCUTANEOUS FAT DEPOSITS BY ELECTROPORATION WITH IMPROVED COMFORT OF PATIENTS

(75) Inventors: Victor I. Chomenky, Minnetonka, MN (US); Ali Jaafar, Eden Prairie, MN (US)

(73) Assignee: Minnesota Medical Physics, LLC, Eden Prairie, MN (US)

(*) Notice: Subject to any disclaimer, the term of this patent is extended or adjusted under 35 U.S.C. 154(b) by 0 days.

(21) Appl. No.: 10/364,187

(22) Filed: Feb. 11, 2003

(65) Prior Publication Data

US 2003/0149451 A1 Aug. 7, 2003

Related U.S. Application Data

(63) Continuation-in-part of application No. 09/931,672, filed on Aug. 17, 2001.
(60) Provisional application No. 60/355,970, filed on Feb. 12, 2002.

(51) Int. Cl.[7] ................................................. A61N 1/18
(52) U.S. Cl. .............................. 607/2; 607/46; 607/63; 607/74
(58) Field of Search ........................... 607/2, 3, 72–74, 607/48, 46, 63; 128/907; 604/20

(56) References Cited

U.S. PATENT DOCUMENTS

| 5,458,625 | A | | 10/1995 | Kendall |
| 5,778,894 | A | * | 7/1998 | Dorogi et al. ............... 128/898 |
| 5,782,882 | A | | 7/1998 | Lerman et al. |
| 5,810,762 | A | * | 9/1998 | Hofmann ..................... 604/20 |
| 6,326,177 | B1 | * | 12/2001 | Schoenbach et al. ..... 435/173.7 |
| 6,349,233 | B1 | | 2/2002 | Adams |
| 6,351,674 | B2 | | 2/2002 | Silverstone |

OTHER PUBLICATIONS

Campbell, N. A., Reece J.B., Mitchell L.G. "Biology" (fifth edition), 1999,Addison Wesley Longman, I.
Russell Hobbie, "Intermediate Physics for Medicine and Biology" (third edition), 1997, Springer–Verl.

* cited by examiner

*Primary Examiner*—Jeffrey R. Jastrzab (57) ABSTRACT

An apparatus and method for non-invasive treatment in lieu of cosmetic surgery is disclosed. The apparatus comprises a combination of a high and low voltage pulse generators connected to two or more electrodes placed on a treatment site of the patient's body. High voltage pulses, delivered to the electrodes, create an electric field that kills subcutaneous fat cells. Low voltage pulses, delivered to the same or individual electrodes provide transcutaneous electrical nerve stimulation (TENS), blocking the signals of discomfort or pain that may arise from the high voltage pulsing.

22 Claims, 7 Drawing Sheets

APPARATUS AND METHOD FOR REDUCING SUBCUTANEOUS FAT DEPOSITS BY ELECTROPORATION WITH IMPROVED COMFORT OF PATIENTS

The present application claims priority from and is a continuation-in-part of U.S. patent application Ser. No. 09/931,672, filed Aug. 17, 2001, entitled Apparatus and Method for Reducing Subcutaneous Fat Deposits, Virtual Face Lift and Body Sculpturing by Electroporation, the specification and drawings of which are incorporated herein in their entirety by reference. The present application also claims priority from U.S. Provisional Patent Application Serial No. 60/355,970, filed Feb. 12, 2002, and entitled Apparatus and Method for Reducing Subcutaneous Fat Deposits by Electroporation with Improved Comfort of Patients, the specification and drawings of which are incorporated herein in their entirety by reference.

1. FIELD OF INVENTION

The present invention relates generally to electroporation in-vivo and specifically to apparatus and method for reducing subcutaneous fat deposits and/or for performing virtual face lifts and/or body sculpturing.

2. BACKGROUND OF INVENTION

"Cosmetic surgery" is a phrase used to describe broadly surgical changes made to a human body with the usual, though not always, justification of enhancing appearance. This area of medical practice constitutes an ever-growing industry around the world. Obviously, where such a procedure fails to deliver an enhanced appearance, the procedure fails to meet the desired goal. One of the reasons that the majority of current procedures fail to deliver upon their promise is that, for the most part, current procedures are invasive, requiring incisions and suturing, and can have serious and unpleasant side effects, including but not limited to scarring, infection, and loss of sensation.

One of the more common forms of cosmetic surgery is the "face-lift." A face-lift is intended to enhance facial appearance by removing excess facial skin and tightening the remaining skin, thus removing wrinkles. A face-lift is traditionally performed by cutting and removing portions of the skin and underlying tissues on the face and neck. Two incisions are made around the ears and the skin on the face and neck is separated from the subcutaneous tissues. The skin is stretched, excess tissue and skin are removed by cutting with a scissors or scalpel, and the skin is pulled back and sutured around the ears. The tissue tightening occurs after healing of the incisions because less skin covers the same area of the face and neck and also because of the scars formed on the injured areas are contracting during the healing process.

Traditional face-lift procedures are not without potential drawbacks and side effects. One drawback of traditional cosmetic surgery is related to the use of scalpel and scissors. The use of these devices sometimes leads to significant bleeding, nerve damage, possible infection and/or lack of blood supply to some areas on the skin after operation. Discoloration of the skin, alopecia (boldness), is another possible side effect of the standard cosmetic surgery. The overall quality of the results of the surgery is also sometimes disappointing to the patients because of possible overcorrections, leading to undesired changes in the facial expression. Additionally, face-lift procedures require a long recovery period before swelling and bruising subside.

The use of lasers to improve the appearance of the skin has been also developed. Traditional laser resurfacing involves application of laser radiation to the external layer of the skin—the epidermis. Destruction of the epidermis leads to rejuvenation of the epidermis layer. The drawback of the laser resurfacing procedure is possible discoloration of the skin (red face) that can be permanent.

Another laser procedure involves using optical fibers for irradiation of the subcutaneous tissues, such as disclosed in U.S. Pat. No. Re36,903. This procedure is invasive and requires multiple surgical incisions for introduction of the optical fibers under the skin. The fibers deliver pulsed optical radiation that destroys the subcutaneous tissues as the tip of the fiber moves along predetermined lines on the face or neck. Debulking the subcutaneous fat and limited injury to the dermis along the multiple lines of the laser treatment results in contraction of the skin during the healing process, ultimately providing the face lift. The drawback of the method is its high price and possibility of infection.

Electrosurgical devices and methods utilizing high frequency electrical energy to treat a patient's skin, including resurfacing procedures and removal of pigmentation, scars, tattoos and hairs have been developed lately, such as disclosed in U.S. Pat. No. 6,264,652. The principle drawback of this technology is collateral damage to the surrounding and underlying tissues, which can lead to forming scars and skin discoloration.

Other forms of cosmetic surgery are also known. One example is liposuction, which is an invasive procedure that involves inserting a suction device under the skin and removing fat tissues. As with other invasive surgical procedures, there is always a risk of infection. In addition, because of the invasive nature of the procedure, physicians usually try to minimize the number of times the procedure must be performed and thus will remove as much fat tissue as possible during each procedure. Unfortunately, this procedure has resulted in patient deaths when too much tissue was removed. Assuming successful removal of excess fat tissue, further invasive surgery may be required to accomplish desired skin tightening.

The prior art to date, then, does not meet the desired goal of performing cosmetic surgery in a non-invasive manner while causing minimal or no scarring of the exterior surface of the skin and at the same time resulting in the skin tightening.

The term "electroporation" (EP) is used herein to refer to the use of a pulsed electric field to induce microscopic pores in the membranes of living cells. Living cells include a biological membrane, also commonly called a cell wall, that separates the inner volume of a cell, or cytosol, from the extracellular space, which is filled with lymph. This membrane performs several important functions, not the least of which is maintaining gradients of concentration of essential metabolic agents across the membrane. This task is performed by active protein transporters, built in the membrane and providing transport of the metabolites via controlled openings in the membrane. Inducing relatively large pores in the cell membrane by electroporation creates the opportunity for a fluid communication through the pores between the cytosol and the extracellular space that may lead to a drastic reduction of these vitally important gradients of concentrations of the metabolic agents. Uncontrolled exchange of metabolic agents, such as ions of sodium, potassium, and calcium between a living cell and the extracellular space imposes on the cell intensive biochemical stress.

When a cell is undergoing biochemical stresses the major biochemical parameters of the cell are out of equilibrium and the cell cannot perform its routine functions. In an attempt to repair itself, the cell starts worling in a damage control mode. The active protein transporters, or pumps, routinely providing transport of various metabolic agents, especially proteins, across membranes, use the energy of hydrogen or sodium positive ions passing from a positive potential of the intracellular space to a negative potential of the cytosol, or for the opposite direction the energy of a negative chlorine ion. This energy supply is provided by maintaining the potential difference across the membrane which, in turn, is linked to the difference in concentrations of sodium and potassium ions across the membrane. When this potential difference is too low, thousands of the active transporters find themselves out of power. Invasion of very high concentration of calcium ions from the interstitial space between cells, where the calcium ion concentration is about 100 times higher than in the cytosol, triggers an emergency production of actin filaments across the large pores in the membrane in an attempt of the cell to bridge the edges of the pores, pull the edges together, and thereby seal the membrane. In muscle cells the calcium ion invasion may cause lethal structural damage by forcing the cell to over-contract and rupture itself. Small pores in the membrane created by a relatively short electric pulse can reseal themselves spontaneously and almost instantaneously after the removal of electric field. No significant damage to the cell is done in this case. Contrary to that, larger pores may become meta-stable with very long life time and cause irreversible damage. It can be said that, depending on the number, effective diameter and life time of pores in the membrane, electroporation of the cell may result in significant metabolic or structural injury of the cell and/or its death. The cause of cell death after electroporation is believed to be an irreversible chemical imbalance and structural damage resulted from the fluid communication of the cytosol and the extracellular environment.

Below a certain limit of the electric field no pores are induced at all. This limit, usually referred to as the "lower EP limit" of electroporation, is different for different cells, depending, in part, on their sizes in an inverse relationship. That is, pores are induced in larger cells with smaller electric fields while smaller cells require larger electric fields. Above the lower EP limit the number of pores and their effective diameter increase with both the amplitude and duration of the electric field pulses.

Removing the electric field pulses enables the induced pores to reseal. This process of resealing of the pores and the ability of the cell to repair itself, discussed briefly above, currently is not well understood. The current understanding is that there is a significant range of electric field amplitudes and pulse durations in which cells survive electroporation and restore their viability thereafter. An electroporated cell may have open pores for as long as many minutes and still survive. The range of electric field amplitudes and pulse durations in which cells survive is successfully used in current biomedical practice for gene transfer and drug delivery inside living cells.

Nevertheless, the survivability of electroporated cells is limited. As the electric field amplitude and/or duration of pulses, increases, this limit, usually referred to as the "upper EP limit" of electroporation, is inevitably achieved. Above the upper EP limit, the number and sizes of pores in the cellular membrane become too large for a cell to survive. Multiple pulses cause approximately the same effect on the cells as one pulse with duration equal to the total duration of all applied pulses. After application of an electrical pulse above the upper electroporation limit the cell cannot repair itself by any spontaneous or biological process and dies. The upper EP limit is defined by the combinations of the amplitudes of electric field and pulse durations that cause cellular death.

The vulnerability of cells to electroporation depends on their size: the larger the cell, the lower the electric field and duration of a pulse capable of killing it. If cells of different sizes are exposed to the same electric field, the largest cells will die first. Thus, this ability of electroporation to discriminate cells by their sizes may be used to selectively kill large cells in the human body.

In the previously referred to application for United States patent application entitled "Apparatus and Method for Reducing Subcutaneous Fat Deposits, Virtual Face Lift and Body Sculpting by Electroporation", Ser. No. 09/931,672, filed Aug. 17, 2001, an apparatus and method for performing non-invasive treatment of the human face and body by electroporation in lieu of cosmetic surgery is disclosed. The apparatus comprises a high voltage pulse generator and an applicator having two or more electrodes utilized in close mechanical and electrical proximity with the patient's skin to apply electrical pulses thereto. The applicator may include at least two electrodes with one electrode having a sharp tip and another having a flat surface. High voltage pulses delivered to the electrodes create at the tip of the sharp electrode an electric field high enough to cause death of relatively large subcutaneous fat cells by electroporation. Moving the electrode tip along the skin creates a line of dead subcutaneous fat cells, which later are metabolized by the body. Multiple applications of the electrode along predetermined lines on the face or neck create shrinkage of the skin and the subcutaneous fat reduction under the treated area.

The electroporation in-vivo, employed in the disclosed method of treatment of subcutaneous fat, involves high voltage pulses applied to the skin of a patient. Delivery of such pulses, however, may result in the patient experiencing an unpleasant sensation of small, but palpable electric jolt or shock during pulsing.

The electric current passing the skin and surrounding tissues between electrodes excites sensory nerves and may cause a discomfort sensation or even pain. This perception is the end result of a process that begins with stimulation of a peripheral sensory nerve and culminating in the conscious awareness of the pain at the cerebral cortex. There are several levels of organization within the central nervous system at which the perception of pain may be interrupted, thereby providing the opportunity to prevent the sensation of pain by a patient.

The perception of pain begins with stimulation of a distal peripheral sensory nerve. The stimulation signal travels to a higher level of sensory collection, which is at the dorsal sensory nerve root ganglion just laterally of the spinal cord. The signal enters the spinal cord and ascends to the brain stem, from which it traverses onto the sensory strip along the cerebral cortex. Each area of the cortex in this strip represents a surface area of the body in a fashion known as the homunculus distribution of the cerebral cortex.

Various procedures and drugs have been employed in the past to interrupt the perception of pain at these various levels. Peripheral nerve blockade is achieved through various methods, the most common of which is a local nerve block with medications such as lidocaine injected at the procedure site.

A variety of medications can be used in local, regional and general anesthesia. Drugs are available for local tissue injection providing a direct anesthetic block at the sensory nerve ends. Other drugs are used for intravenous delivery and disseminate throughout the entire body and produce a general anesthesia effect. Intermediate to this, medications have been developed for direct injection into nerve bundles to provide a regional type of anesthetic block. Such examples of regional anesthesia are axillary nerve blocks putting the arm to sleep, sacral nerve blocks putting the back of the leg to sleep, and saddle blocks or epidural blocks that render the entire lower half of the body anesthetized.

Anesthetic drugs are efficient in reducing or blocking the sensation of pain, but they have their own drawbacks. They can have toxic side effects or cause allergic reactions in certain patients. Also, they can significantly increase the cost of surgical or other procedures. Whenever it is possible, it is desirable to avoid usage of the pharmacological drugs for pain control.

The Gate Control Theory of pain was initially proposed in 1965 by Melzack and Wall and now is widely accepted by the scientific community. The Gate Control Theory provides that large and small diameter nerve fibers, both of which carry pain signals, travel through the same "gate mechanism." The theory further provides that activated large nerve fibers can inhibit the transmission of a pain signal by the smaller nerves fibers.

Chemicals released as a response to the pain stimuli also influence whether the gate is open or closed for the brain to receive the pain signal. This lead to the theory that the pain signals can be interfered with by stimulating the periphery of the pain site, the appropriate signal-carrying nerves at the spinal cod, or particular corresponding areas in the brain stem or cerebral cortex. It is generally recognized that the "Pain Gate" can be shut by stimulating nerves responsible for carrying the touch signal (mechanoreceptors). This finding enables the relief of pain through massage techniques, rubbing, and also the application of hot wheat bags or cold ice packs. The Gate can also be shut by stimulating the release of endogenous opioid-type chemicals that are released by the body in response to the pain stimuli.

One of non-drug mediated pain control techniques is called Transcutaneous Electrical Nerve Stimulation (TENS). It is based on a discovery that application of electrical current to the body can also interfere with transmission of pain signals along the nerve pathways and give patients a significant analgesic (pain relieving) effect. The Gate Control Theory of pain suggests that this effect is mediated by endogenous pain relieving chemicals, released by the body in response to the electric transcutaneous stimulation, consequently blocking the ability of the nerve to transmit pain signals. If a large nerve, responsible for transmission of perception of heat or touch, is carrying periodic signals from the endings on the skins, the Gate for the pain signals transmitted to the spinal cord via small nerves are closed and the pain is reduced.

Currently TENS is used primarily for symptomatic relief and management of chronic intractable pain or as an adjunctive treatment in the management of post-surgical or post-traumatic acute pain. TENS usually involves the application of a sequence of short electrical pulses with relatively low repetition rate intended to affect the nervous system in such a way as to suppress the sensation of pain from acute or chronic injury. Typically, two electrodes are secured to the skin at appropriately selected locations. Mild electrical impulses are then passed into the skin through the electrodes to interact with the underlying nerves over the treatment site. As a symptomatic treatment, TENS has proven effective in the reduction of both chronic and acute pain of patients.

It would be desirable to have a method and apparatus that could mitigate the discomfort created by the electroporation in-vivo without resorting to anesthetic drugs using non-pharmocological aids.

3. SUMMARY OF THE INVENTION

The present invention provides an apparatus and method for creation of a controlled injury or alteration to the subcutaneous tissue and/or underside of the dermis, with the following healing process leading to the contraction of the skin; and/or to the controlled destruction of fat cells, leading to their permanent loss, all with increased comfort for the patient. In the present invention the damage to the subcutaneous tissue, underside of the dermis, and/or fat cells is caused by electroporation. Patient discomfort associated with using electroporation in-vivo for cosmetic purposes is attacked by an apparatus and a method according to the present invention. To do so, apparatus and method relating to TENS is incorporated into the electroporation apparatus used for reducing subcutaneous fat deposits, virtual face lift and body sculpturing to relieve a discomfort that may arise from electroporation treatment. The new apparatus is provided with an additional low voltage pulse generator connected to electrodes placed on a treatment site of the patient's body. Improved comfort for the patients is achieved by delivering a sequence of low voltage pulses that provide transcutaneous electrical nerve stimulation, thereby substantially blocking the neural messages of discomfort or pain that may arise from the high voltage pulsing. To create some initial analgesic effect, a sequence of TENS pulses may be applied before delivery begins of an electroporation pulse, with the TENS pulses continuing for some time after. The analgesic effect is mediated by a release of natural body analgesics triggered by TENS.

Another feature of the current invention is that the electroporation pulses delivered to the treatment site are synchronized with the TENS pulses. Thus, each electroporation pulse may be applied with a delay after a TENS pulse, namely during a refractory period for the surrounding nerves caused by the TENS pulse. The refractory period is a state of a nerve cell that exists for a short period of time after the onset of an excitation, approximately 0.5 milliseconds, and is characterized by an absolute inability of the nerve to be excited by a stimulus, no matter how intense this stimulus is. This is so called "absolute refractory period". In the next 1.0 ms the ability of the nerve to be excited gradually returns to a normal level, but the threshold of excitation during this period is significantly higher than its normal level. This is the so-called "relative refractory period". Thus, according to the current invention, the high voltage pulses are applied to the patient's skin only when all or substantially all of the nerves surrounding the treatment site are in the refractory state created by a previous application of a TENS pulse. Application of EP pulses during the refractory period will provide significant improvement of the patient's comfort during an electroporation procedure.

The present invention, as well as its various features and advantages, will become evident to those skilled in the art when the following description of the invention is read in conjunction with the accompanying drawings and claims. Throughout the drawings, like numerals refer to similar or identical parts.

5. DESCRIPTION OF THE INVENTION

Figure 1:
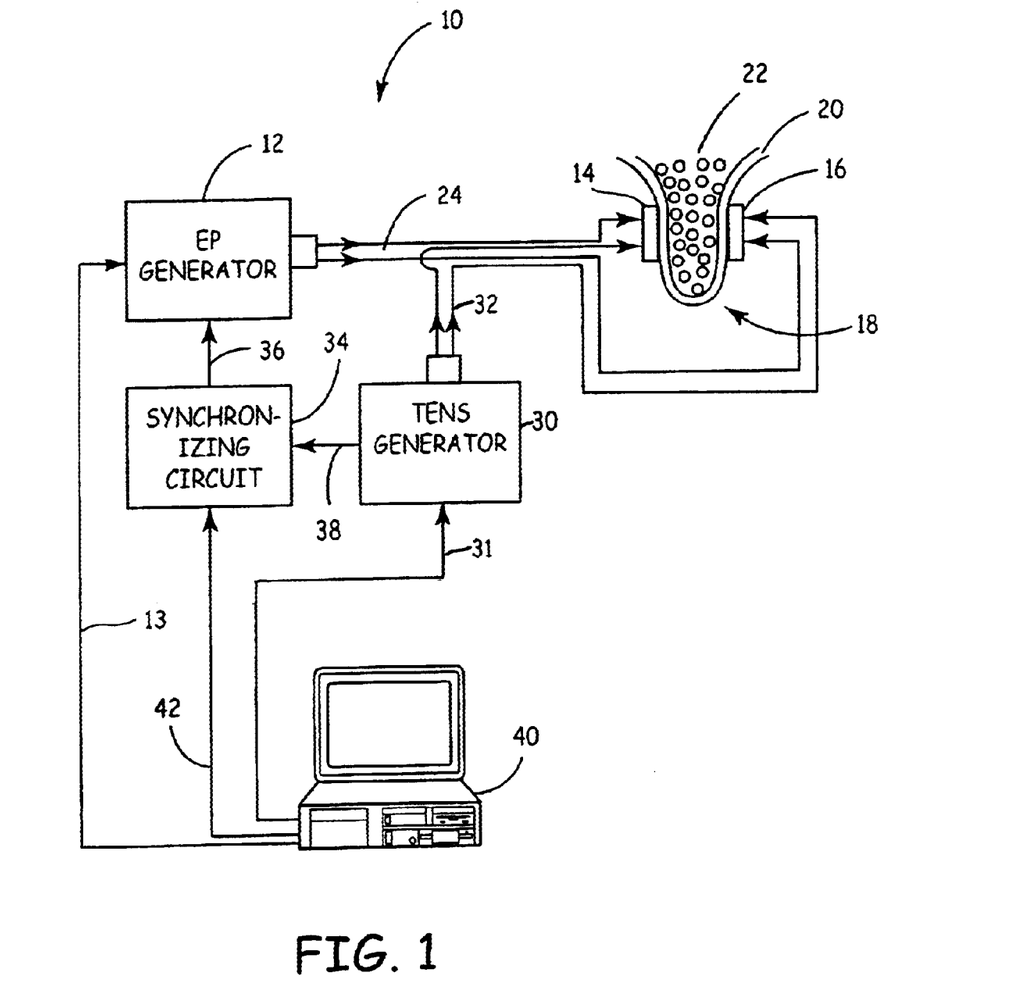
FIG. 1 is a schematic illustration of an electroporation system for cosmetic treatment with improved patient's comfort.

FIG. 1 shows schematically an electroporation system 10 for in-vivo treatment of subcutaneous fat deposits and tightening of the skin. The system includes a high voltage electroporation pulse generator 12 and electrode sets (or arrays of electrodes) 14 and 16. The electrodes may be applied to a fold 18 of a patient's skin 20 with subcutaneous fat deposit 22 at a selected location on the patient's body for the purpose of applying electroporation therapy thereto. The high voltage electroporation pulses from generator 12 are delivered to the electrodes 14 and 16 via a multiple conductor cable 24. The electrodes 14 and 16 and the cable 24 may be secured to a hand held applicator adapted for manipulation of the electrodes on the patient's skin during EP treatment (not shown in the FIG. 1).

System 10 further includes a TENS generator 30 that is connected to the electrodes 14 and 16 via an appropriate connector 32. A synchronizing circuit 34 may be provided to introduce a controllable time delay of high voltage EP pulses provided by the generator 12 to the electrode sets 14 and 16 relative to the sequence of TENS pulses provided by the generator 30 to the electrode sets 14 and 16. Synchronizing circuit 34 may be connected to generator 12 by an appropriate connector 36 and to generator 30 by an appropriate connector 38. This time delay may fall within a range of about 0.1 to about 1.5 milliseconds.

A computer 40 connected by an appropriate connector 42 to synchronizing circuit 34, by a connector 13 to EP generator 12, and by a connector 31 to TENS generator 30 may be provided to control the whole procedure of EP treatment: the predetermined amplitude, duration, and number of EP and TENS pulses and the sequencing EP and TENS pulses supplied to the electrodes 14 and 16. To alleviate discomfort, the TENS system generates trains of nerve stimulation pulses which are applied to the patient's skin 20. In an embodiment of the present invention TENS system generator 30 may generate pulses with a repetition rate 40–200 Hz, with each nerve stimulation pulse having a duration of approximately 20–1000 microseconds and a current peak of approximately 0.100 A. The EP pulses may be applied with a repetition rate of 1 to 50 Hz and may have a current peak of 0.5–10 A depending on the size and shape of electrodes or electrode arrays. Generally, the voltage of the EP pulses can be in the range of 50 V to 5000 V with a duration from 10 microseconds to 1.0 milliseconds depending on the location of the treated segment of the body, the sizes and shapes of the electrodes, and the distance between the electrodes. Regardless of the possible configuration of the electrodes and the voltages applied to the treatment volume, the voltage applied to an individual subcutaneous fat cell should fall in the range of 2 to 5 V per cell to be able to kill it.

In one embodiment of the present invention the TENS pulses are applied to the same electrodes as the EP pulses. In another embodiment TENS pulses and EP pulses are applied to different electrodes (or arrays of electrodes) placed close to each other and to the EP electrodes. The EP electrodes may be a set of relatively sharp needles. The sharp electrodes provide enhancement of the electric field necessary for efficient EP treatment of the skin cells, which are significantly smaller than the subcutaneous fat cells (5 micron diameter versus 100 micron for fat cells). To be efficient in patient pain and discomfort reduction, the TENS pulses should be applied to a more extended skin area than the EP pulses. This extended coverage area is desirable so that the TENS pulses are able to excite the large nerve fibers that are responsible for the heat and touch sensations on the skin, the excitation of which actually blocks the transmittance of the pain signals. These large nerve fibers are densely distributed under the skin across the body and can be easily excited by wider electrodes positioned adjacent to or around the EP electrodes. In the embodiment of the invention in which all electrodes are common for both type of pulses, or only two electrodes are employed, the amplitude and duration of TENS pulses should be high enough to excite all the nerves around the electrodes that can be excited by the EP pulses. The delay time between a TENS and an EP pulses in this case generally may be longer than in the case of separate TENS electrodes covering a larger area. The longer delay is beneficial because the nerve excitation caused by the TENS pulse propagates around the electrode with velocity of about 4 meters per second and increases the area affected by the TENS pulse by a margin of 2 mm for the delay of 0.5 millisecond. For a needle type electrode with a diameter of the tip less than 1 mm, this 2 mm margin is significant for reducing sensation of the EP pulse by the patient. If desired, the actual optimal delay may be determined during a procedure by a physician using a feedback for sensation of discomfort experienced by the patient.

To provide the anesthetic effect the TENS system preferably should be "on" continuously during the EP treatment or at least start for some time before the EP treatment.

Figure 2:
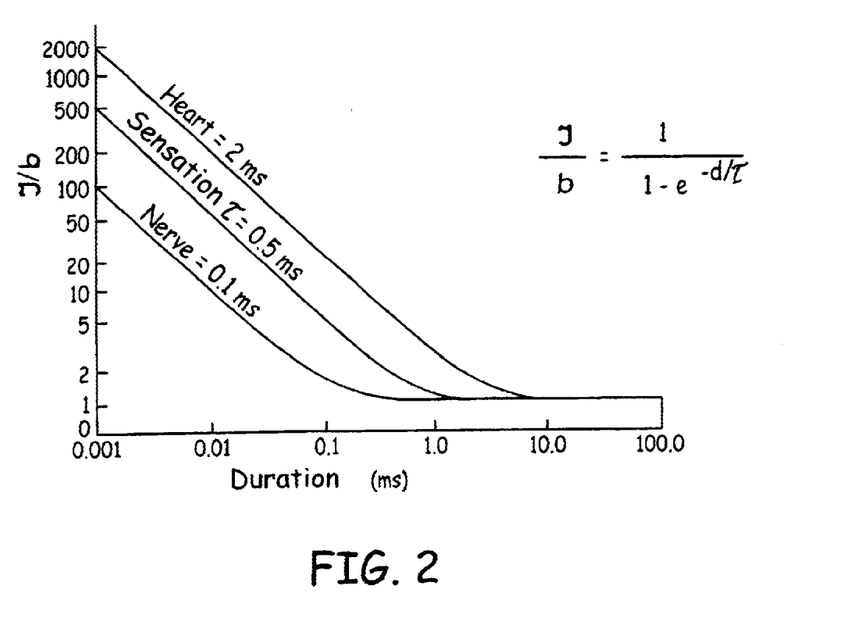
FIG. 2 shows the strength-duration curve for excitation of a nerve.

To achieve successful cell killing by electroporation the electric field applied to the treated volume of cells must be above the upper EP limit for the cells. The probability of cell killing increases if longer or multiple pulses are employed. As far as the sensation of electrical pulses by the patient is concerned, it also varies with duration. The general law is: the longer pulse is, the stronger the sensual response of the patient is. The mathematical equation for this law, usually referred to as the "strength—duration curve", was discovered by Blair in 1932. The strength-duration curve is applicable to rectangular pulses and describes the excitation current density I (mA/cm$^2$) as a function of pulse duration d:

$$I=b/(1-e^{-d/\tau});$$

where:
d=the pulse duration;
b=the threshold excitation current density for an infinitely long pulse;
I=the threshold excitation current density for a pulse with duration d; and
τ=the membrane time constant for a particular excitable tissue.

For sensory nerves in the human skin, τ▽0.5 ms (millisecond) and b▽2 (mA/cm$^2$). The strength-duration curves illustrating the Blair equation for different excitable tissues are shown in FIG. 2. The middle curve in the figure shows the strength-duration curve for the excitation of sensory nerves which are located in the skin and are responsible for the sensation of discomfort during electroporation procedure. The curves illustrate the relative increase in the threshold of excitation with the decrease in the duration of the electrical pulses for different excitable tissues. As can be seen from the middle curve, the threshold of excitation of sensory nerves (the middle curve of the three shown on the Figure) for 10–20 microsecond pulses is 20–50 times higher than that for 1 ms pulses. Electroporation is observed where the applied pulses have a duration of 10 microseconds and longer. To preserve the ability of EP pulses to kill cells but at the same time create as low of a sensation as possible in the patient, relatively shorter multiple pulses are preferred to long EP pulses. To preserve the ability to excite nerve cells in the extended area around electrodes, which is especially important when the same electrodes are used for both type of pulsing, the TENS pulses, having lower amplitudes than the EP pulses, may be selected to be significantly longer than the EP pulses, but at lower amplitudes than the EP pulses.

Figure 3:
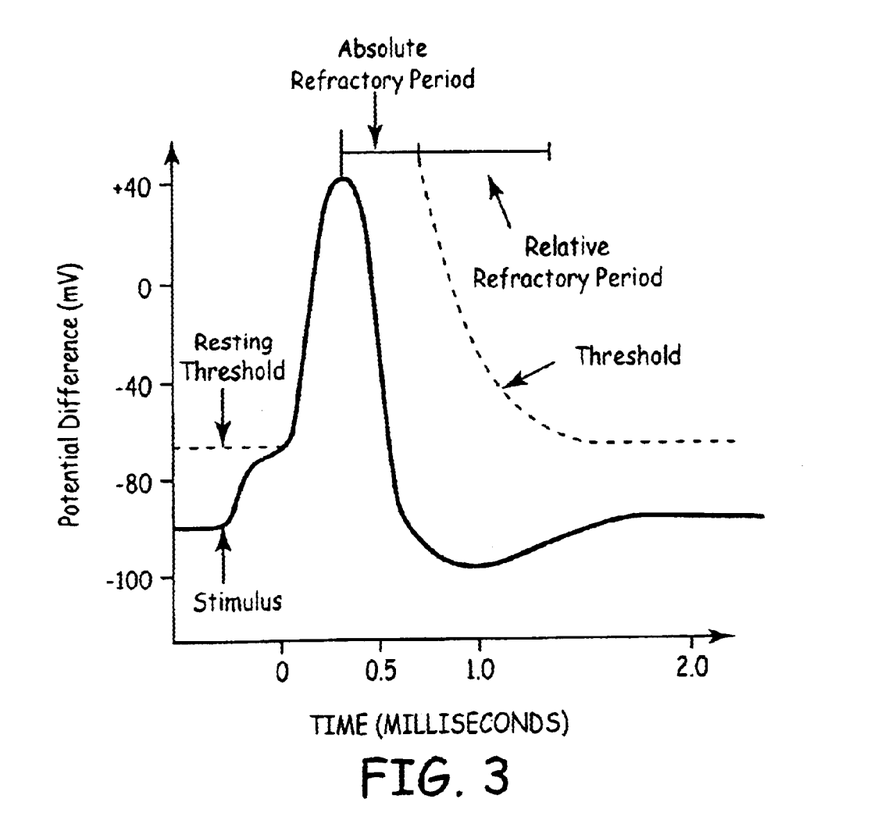
FIG. 3 is an illustration of an action potential and excitability of a nerve.

An excitation threshold of a nerve depends not only upon the duration of the stimulating pulse but also upon the immediate local excitation history of the nerve. FIG. 3 shows a plot of an "action potential," which is a potential difference between the inner and the outer sides of the cell membrane as a function of time during an excitation. Normally, when a cell is at rest, the potential difference (or as commonly called, the voltage) across the membrane, called a "resting potential," is about −90 mV. When an electric stimulus causes local depolarization of the membrane (decreases the negative potential across the membrane) to a value about −60 mV, called a "resting threshold", the cell gets excited and an action potential starts propagating from the site of excitation along the nerve fiber. That is, as the potential difference across the membrane exceeds the resting threshold, a sudden change in the permeability of the membrane for sodium and potassium ions ($Na^+$ and $K^+$, respectively) occurs that causes rapid movement of these ions across the cell membrane, resulting in the action potential. The action potential propagates along the cell and depending on where it goes and where it comes from, carries different signals in the body.

As can be seen from the FIG. 3, over a period of time of about 1.5 ms the potential across the cell membrane rapidly increases from its resting threshold of about −60 mV to +40 mV and slowly returns back to the resting potential of −90 mV. There is a period of about 0.75 ms after stimulation when the nerve cannot be restimulated at all, no matter how high the stimulus is. This period is called the "absolute refractory period" (the threshold is infinitely high) and generally lasts for approximately 0.75 ms after reaching the peak of the action potential at about +40 mV. The absolutely refractory period is followed by a "relative refractory period", where a stimulus greater than normal is needed to initiate an action potential. The evolution of the level of the excitation threshold during an action potential is shown in FIG. 3 by a dashed line.

The threshold of excitation of a cell at rest depends not only on the duration of the electrical stimulus but also on the waveform of the stimulus. The threshold for a bipolar pulse, consisting of two parts, a positive one and identical in shape but negative in polarity, is higher than that for a unipolar pulse. The reason for that is that the cell launches an acting potential only when the resting threshold of the excitation is reached. This happens when a change of the electrical charges on both sides of the membrane occurs that depolarizes it from −90 mV to −60 mV. If a bipolar pulse is applied to the cell, only the first half of the pulse causes a depolarization of the cellular membrane that can lead to a firing of an action potential. If the cell is not ready to fire after the first half of the pulse, when the current reverses and begins to flow the other direction in the second half of the pulse, the reversing electric current polarizes the membrane back to the previous level of −90 mV. In other words, all nerves including sensory are less sensitive to bipolar pulses than to unipolar of the same overall duration. Actually, their sensitivity approximately corresponds to that of a unipolar pulse with a half duration.

Bipolar rectangular pulses are known to be very efficient in cell killing by electroporation. Contrary to the sensitivity of excitable cells to electric stimulus, both directions of the electrical field, that is, positive (+) and negative (−), are equally efficient in creating pores in cellular membranes. This efficiency results because electroporation is a process is related to the difference in the energy of the porous and non-porous membrane in the presence of an electric field. This energy difference depends on the square of the amplitude (or strength) of the electric field (i.e., $E^2$) and does not depend on the sign or polarity (+ or −) of the electric field.

From a practical stand point, however, applying balanced pulses during in-vivo electroporation treatment has one important advantage. Contrary to unipolar pulsing, that carries a direct current component into the treated tissue and creates undesired electrolytic effects on the interface of the electrodes and tissues, bipolar pulsing is free from these drawbacks. With the bipolar pulsing problems such as metal depositions from the electrodes or chemical decomposition of tissue during treatment are largely if not completely avoided.

These advantageous properties of balanced pulses, namely, lower excitability of the nerve cells, high efficiency in cell killing and freedom from electrolytic effects, make using rectangular bipolar balanced pulses a preferred mode for electroporation pulsing in the current invention. Technically, balancing of two pulses of the opposite polarities may be easily achieved by using a pulse generator having a direct current blocking capacitor electrically coupled in series to the transcutaneous electrodes.

Figure 4A:
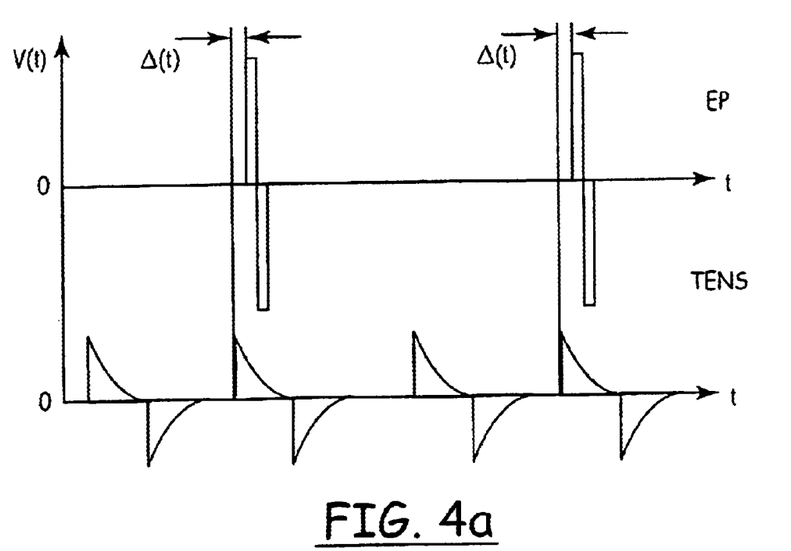
FIGS. 4a and 4b are time diagrams of electric pulses applied to the electrodes.
Figure 4B:
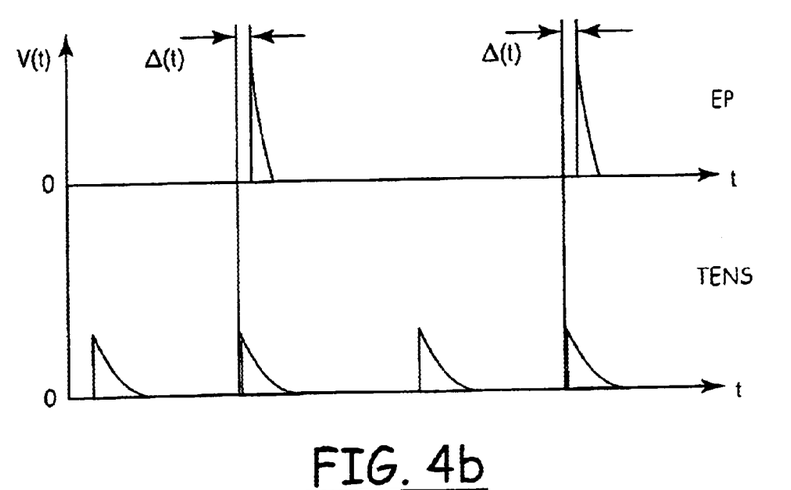

The time diagram of the pulses applied to the electrodes are shown in FIGS. 4a and 4b. In FIGS. 4a and 4b voltage is plotted as a function of time for the In FIGS. 4a and 4b voltage is plotted as a function of time for the EP pulses designated for cell killing (the upper curve in each of FIGS. 4a and 4b), and the TENS pulses applied for mitigation of discomfort of the patient (the lower curve in each of FIGS. 4a and 4b). In FIG. 4a bipolar balanced rectangular EP pulses and exponential balanced TENS pulses are shown. This is the preferred embodiment for the EP—TENS treatment of the current invention. FIG. 4b shows unipolar exponential pulses. The time delay Δt between preselected TENS and synchronized EP is introduced into pulsing to ensure that the high voltage pulses are applied during the refractory state of the surrounding nerves to minimize discomfort of the patient. This time delay falls into a range of 0 to about 1.5 milliseconds and can be selected during the treatment procedure for the best comfort of the patient The EP pulses depend upon the size of the electrodes and the distance between them and may be in the range of about 50 V to about 5000 V with a duration of about 10 microseconds to about 1.0 milliseconds. The TENS pulses may have duration of about 20 to about 1000 microseconds.

Figure 5:
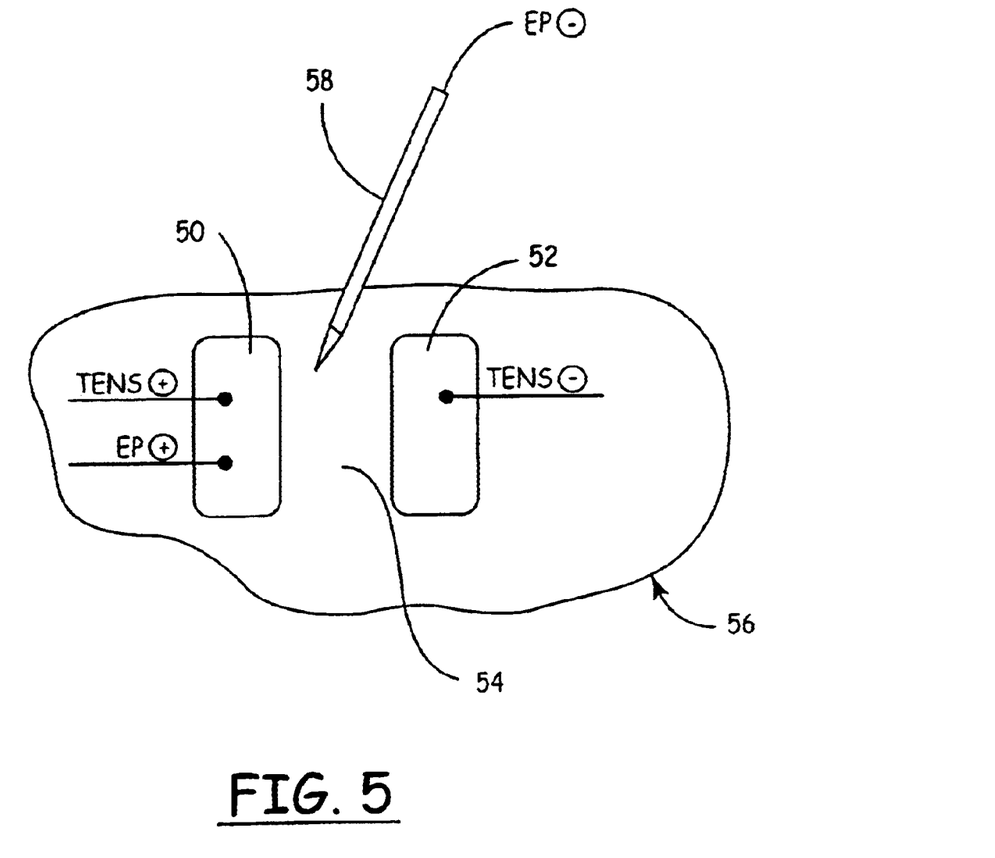
FIG. 5 shows exemplary electrodes for EP treatment combined with TENS.
Figure 6:
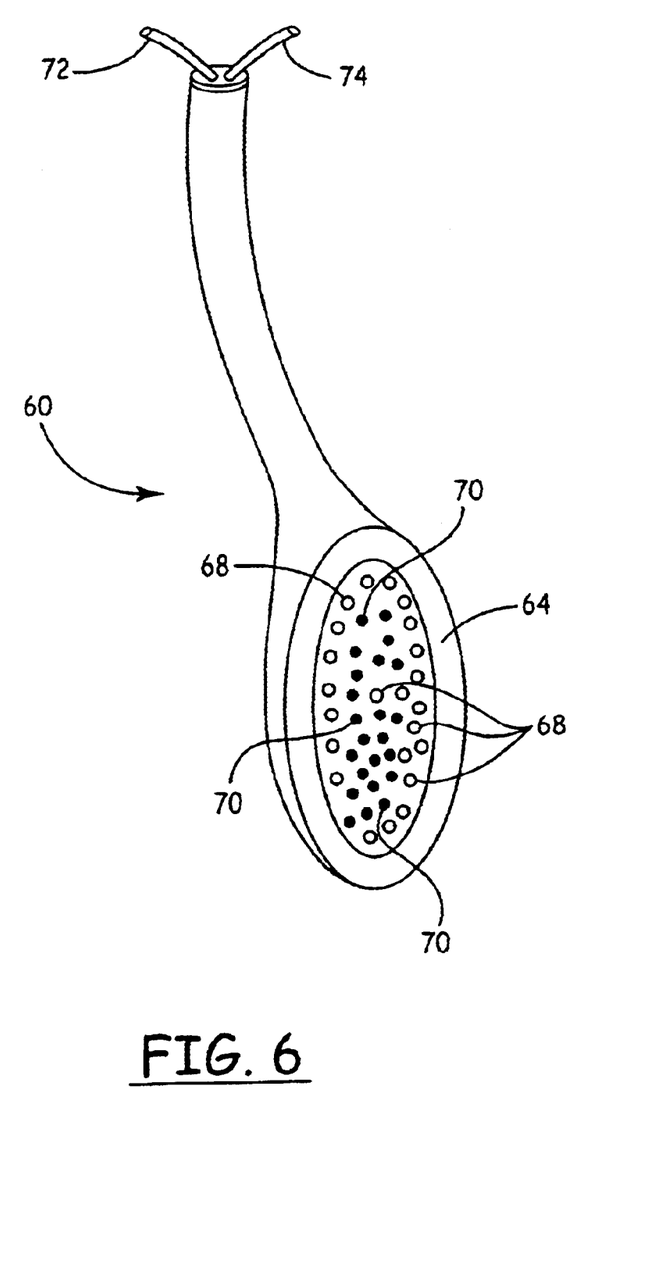
FIG. 6 illustrates another embodiment of an apparatus in accord with the present invention.
Figure 7:
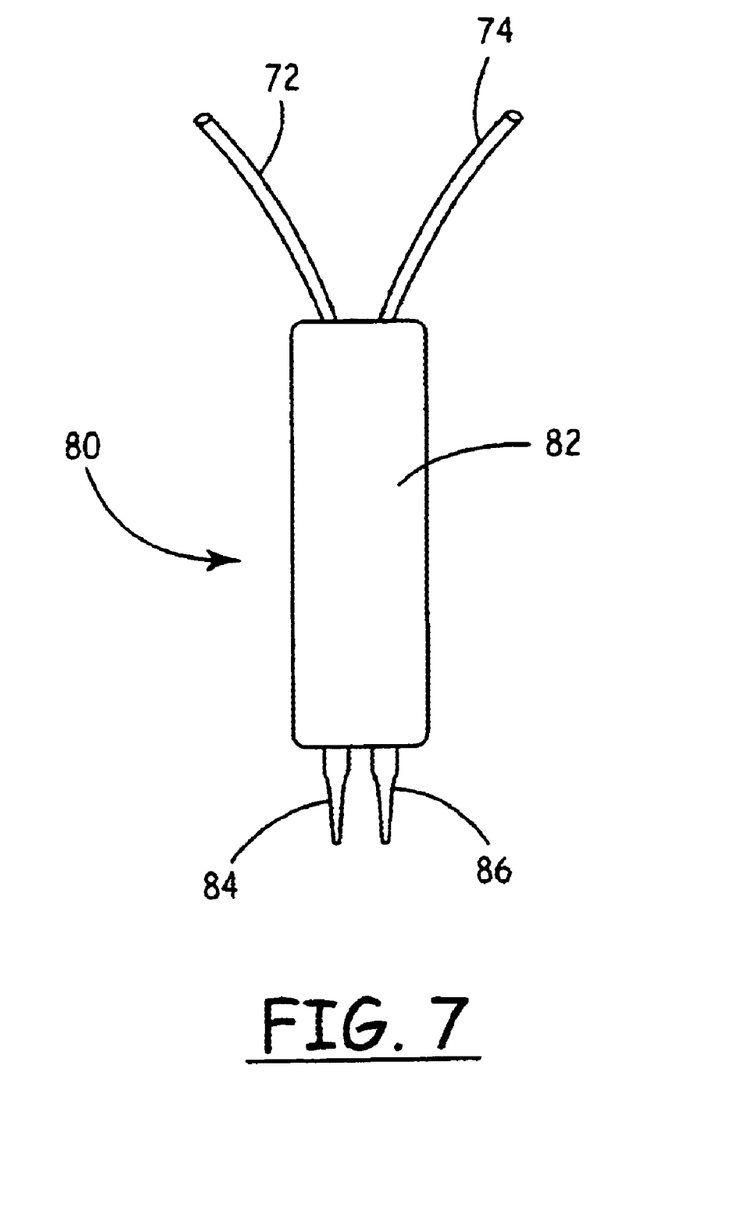
FIG. 7 illustrates yet another embodiment of an apparatus in accord with the present invention.

FIGS. 5–7 show different embodiments of applicators for combining EP and TENS treatment. In FIG. 5 two large pad electrodes, positive 50 and negative 52, provide TENS treatment for the area 54 of the skin 56 between the pads 50 and 52. One electrode of the EP generator, exemplary positive, is connected to pad 50, while the second, negative polarity electrode of the generator is connected to a needle electrode 58, thereby providing EP treatment in the area between the pad electrodes 50 and 52. In this embodiment, the pads would be applied to the skin and held there in a known manner, while the needle electode 58 would me manually or mechanically manipulated as desired in the area between the pads.

In FIG. 6 a multi-needle applicator 60 is shown having a hand piece 62. Handpiece 62 is attached to a frame 64 of a desired configuration carrying a an array of needle electrodes 66 comprising a plurality of needle electrodes 68 and 70. Some of the needle electrodes, those designated as electrodes 68, and which are primarily on the periphery of the array, may be connected to a TENS generator to function as TENS electrodes alone, while needle electrodes 70 may be connected to both the TENS and EP generators to function as both EP and TENS electrodes. It will be observed that placing the combined EP and TENS electrodes 70 inside the periphery of the TENS only electrodes 68 that a TENS coverage area exceeding the EP coverage area is achieved. The appropriate connectors 72 and 74 are used to connect the applicator 60, and thus the needle electrodes 68 and 70, to the EP and TENS generators.

FIG. 7 shows a two electrode applicator 80 including a handle 82. In this embodiment of the present invention, both electrodes 84 and 86 are common for EP and TENS processes. For this embodiment of the applicator the TENS pulses should be selected to be generally longer in duration and higher in the amplitude while the EP pulses should be short and multiple with a relatively long delay time. This choice of operating parameters of the system will ensure that the TENS treatment is provided to the whole area where the EP pulses can possibly excite the sensory nerves.

In operation, apparatus in accord with the present invention will include using TENS electrodes to create an anesthetic effect in at least the treatment volume and preferentially in a larger volume of patient tissue that includes the treatment volume. This anesthetic effect can be created by application of TENS pulses to the patient. Preferably subsequently to the creation of the anesthetic effect, EP pulses can be applied to the treatment, resulting in the death of some or all of the subcutaneous fat cells in the treatment volume. Other patient tissue treatment volumes can then be treated similarly. In this manner then, the present invention provides apparatus and method for reducing subcutaneous fat deposits by electroporation with improved comfort of patients.

The present invention has been described in language more or less specific as to the apparatus and method features. It is to be understood, however, that the present invention is not limited to the specific features described, since the apparatus and method herein disclosed comprise exemplary forms of putting the present invention into effect. The invention is, therefore, claimed in any of its forms or modifications within the proper scope of the appended claims appropriately interpreted in accordance with the doctrine of equivalency and other applicable judicial doctrines.

What is claimed is:

1. An apparatus for reducing subcutaneous fat deposits by electroporation with improved comfort of patients comprising:

an applicator comprising two sets of electrodes, the first and the second, said first set of electrodes are high voltage electrodes adapted for engaging the skin of a patient and applying a high amplitude pulsed electric field to the area of skin and the subcutaneous volume of tissues to be treated by electroporation, said second set of electrodes adapted for transcutaneous electrical nerve stimulation of the skin and the volume of the subcutaneous tissue over an area generally larger than the area of electroporation treatment;

a generator of high voltage pulses for applying pulsed electric field to the first set of electrodes, said pulses generating an electric field above the upper electroporation limit for subcutaneous fat cells in the volume of the subcutaneous tissue to be treated;

a generator for generating low voltage pulses for applying pulsed electric field to the second set of electrodes, said amplitude of the electric field is adapted for Transcutaneous Electrical Nerve Stimulation (TENS) of the skin and subcutaneous tissue;

a synchronizing circuit connected to said high and said low voltage pulse generators and providing triggering of the high voltage pulses with a controllable delay after the TENS pulses, and connectors connecting said generators of high and low voltage electrical pulses with corresponding high and low voltage electrodes.

2. An apparatus according to claim 1 wherein the two sets of electrodes in the applicator share at least some electrodes to which both the high voltage pulses for electroporation and low voltage pulses for TENS are applied.

3. An apparatus according to claim 1 wherein said high voltage pulses have duration in a range of 10 microseconds to 1 millisecond.

4. An apparatus according to claim 1 wherein the amplitude of the electric field applied to the treated volume falls in a range of 20 Volt/mm to 2000 Volt/mm.

5. An apparatus according to claim 1 wherein said delay of the high voltage pulses relatively to the TENS pulses falls into the time range of 0 to 1.5 milliseconds.

6. An apparatus according to claim 1 wherein both low and high voltage pulses are electrically balanced in such a manner that in average no direct current is passing through the treatment volume.

7. An apparatus according to claim 1 wherein high voltage pulses are rectangular balanced.

8. An apparatus according to claim 1 wherein said low voltage pulses have duration in a range of 10 to 200 microseconds.

9. An apparatus according to claim 1 wherein said low voltage pulses have repetition rate in a range of 4 to 120 Hertz.

10. An apparatus according to claim 1 wherein said low voltage pulses have amplitude in the range from 10 to 100 V.

11. A method for reducing subcutaneous fat deposits by electroporation with improved comfort of patients comprising:

providing an applicator comprising first and second sets of electrodes, wherein first set of electrodes are high voltage electrodes are configured for engaging the skin of a patient and applying a high amplitude pulsed electric field to the area of skin and the subcutaneous volume of tissues to be treated by electroporation and wherein said second set of electrodes are configured for transcutaneous electrical nerve stimulation of the skin and the volume of the subcutaneous tissue over an area generally larger than the area of electroporation treatment;

providing a generator of high voltage pulses for applying pulsed electric field to the first set of electrodes, said pulses generating an electric field above the upper electroporation limit for subcutaneous fat cells in the volume of the subcutaneous tissue to be treated;

providing a generator for generating low voltage pulses for applying pulsed electric field to the second set of electrodes, said amplitude of the electric field providing transcutaneous electrical nerve stimulation (TENS) of the skin and subcutaneous tissue;

providing a synchronizing circuit connected to said high and said low voltage pulse generators and providing triggering of the high voltage pulses with a controllable delay after the TENS pulses;

connecting said generators of high and low voltage electrical pulses with corresponding high and low voltage electrodes; and applying TENS pulses via said second set of electrodes to the area in and around of the area to be treated and high voltage pulses via said first set of electrodes with an amplitude sufficient to cause death to subcutaneous fat cells.

12. An apparatus for reducing subcutaneous fat deposits in a predetermined treatment volume beneath a predetermined area of a patient's skin by electroporation with improved comfort for the patient, said apparatus comprises:

first and second electrode sets, wherein said first electrode set comprises:
  at least a pair of electroporation electrodes, said electroporation electrodes being provided for applying a pulsed electric field to the predetermined area of skin and the subcutaneous volume of tissues; and wherein said second electrode set comprises:
  at least a pair of TENS electrodes, said TENS electrodes being configured for transcutaneous electrical stimulation of the patient over a tissue volume including at least the predetermined treatment volume;

a generator of high voltage pulses for applying a pulsed electric field to the predetermined area via said first electrode set, said pulses generating an electric field above the upper electroporation limit for subcutaneous fat cells in the volume of the subcutaneous tissue to be treated;

a generator for generating low voltage pulses for applying a pulsed electric field to the predetermined area via said second electrode set, wherein the amplitude of the low voltage electric field is chosen to provide transcutaneous electrical nerve stimulation (TENS) of the nerves of the skin and subcutaneous tissue in an area larger than the predetermined area;

a synchronizing circuit connected to said high and said low voltage pulse generators and providing triggering of the high voltage pulses with a controllable delay after the TENS pulses, and connectors connecting said generators of high and low voltage electrical pulses with corresponding electroporation and TENS electrodes.

13. An apparatus according to claim 12 wherein the two sets of electrodes in the applicator share at least some electrodes to which both the high voltage pulses for electroporation and low voltage pulses for TENS are applied.

14. An apparatus according to claim 12 wherein said delay of the high voltage pulses relatively to the TENS pulses falls into the time range of 0 to 1.5 milliseconds.

15. An apparatus according to claim 12 wherein both low and high voltage pulses are electrically balanced in such a manner that in average no direct current is passing through the treatment volume.

16. An apparatus according to claim 12 wherein high voltage pulses are rectangular balanced.

17. A method for reducing subcutaneous fat deposits in a treatment volume by electroporation with improved patient comfort, said method comprising:

applying a plurality of electroporation electric field pulses to the treatment volume to induce subcutaneous fat cell death by electroporation; and applying a plurality of TENS electric field pulses at least to the treatment volume to improve patient comfort by transcutaneous electric nerve stimulation at least in the treatment volume.

18. The method of claim 17 wherein the TENS electric field is applied to at least the treatment volume prior to application of the electroporation field.

19. The method of claim 17 wherein the applied electroporation and TENS pulses are synchronized such that a TENS pulse is applied to at least to the treatment volume prior to application of an electroporation pulse.

20. The method of claim 19 wherein application of an electroporation pulse relative to the application of a TENS pulse is delayed by a time in the range of about 0 to about 1.5 milliseconds.

21. The method of claim 17 wherein both electroporation and TENS pulses are electrically balanced in such a manner that in average no direct current is passing through the treatment volume.

22. The method of claim 1 wherein the electroporation pulses are rectangularly balanced.

* * * * *